United States Patent
Yoshida et al.

(10) Patent No.: US 11,237,157 B2
(45) Date of Patent: Feb. 1, 2022

(54) REAGENT AND METHOD FOR ASSAYING THROMBIN-ANTITHROMBIN COMPLEX

(71) Applicant: LSI MEDIENCE CORPORATION, Tokyo (JP)

(72) Inventors: Tatsuya Yoshida, Tokyo (JP); Yuhang Yang, Tokyo (JP)

(73) Assignee: LSI MEDIENCE CORPORATION, Tokyo (JP)

( * ) Notice: Subject to any disclaimer, the term of this patent is extended or adjusted under 35 U.S.C. 154(b) by 0 days.

(21) Appl. No.: 16/861,040

(22) Filed: Apr. 28, 2020

(65) Prior Publication Data

US 2020/0256864 A1 Aug. 13, 2020

Related U.S. Application Data

(62) Division of application No. 15/562,839, filed as application No. PCT/JP2016/060261 on Mar. 29, 2016, now abandoned.

(30) Foreign Application Priority Data

Mar. 31, 2015 (JP) .................. 2015-074168
Mar. 31, 2015 (JP) .................. 2015-074173

(51) Int. Cl.
*G01N 33/53* (2006.01)
*G01N 33/543* (2006.01)

(52) U.S. Cl.
CPC ....... *G01N 33/54333* (2013.01); *G01N 33/53* (2013.01); *G01N 33/5306* (2013.01); *G01N 33/543* (2013.01); *G01N 33/54353* (2013.01); *G01N 2333/974* (2013.01)

(58) Field of Classification Search
CPC ............ G01N 33/54333; G01N 33/53; G01N 33/543; G01N 33/5306; G01N 33/54353; G01N 2333/974
See application file for complete search history.

(56) References Cited

U.S. PATENT DOCUMENTS

2001/0007774 A1  7/2001  Saitoh et al.

FOREIGN PATENT DOCUMENTS

| EP | 0391433 A2 | 10/1990 |
|---|---|---|
| EP | 0669344 A1 | 8/1995 |
| EP | 0669344 A2 | 8/1995 |
| JP | H03-048158 A | 3/1991 |
| JP | H07-238099 A | 9/1995 |
| JP | H07-260788 A | 10/1995 |
| JP | H08-110341 A | 4/1996 |
| JP | H10-026621 A | 1/1998 |
| JP | 2001-228153 A | 8/2001 |
| JP | 2001-289850 A | 10/2001 |
| JP | 2002-316999 A | 10/2002 |

OTHER PUBLICATIONS

Asakura, S., et al., Preparation and Characterization of Monoclonal Antibodies Against the Human Thrombin-Antithrombin III Complex, Biochimica et Biophysica Acta 952(1):37-47, 1988.
Collen, D., et al., Quantitation of Thrombin-Antithrombin III Complexes in Human Blood, European Journal of Clinical Investigation 7(5):407-411, 1977.
Corada etal., Blood, 2001; 97:1679-84.
E. A. Padlan, Adv Prat Chem 49:57-133; 1996.
Elgue, G., et al., The Use of a Commercial ELISA for Assay of Thrombin-Antithrombin Complexes in Purified Systems, Thrombosis and Haemost 63(3):435-438, 1990.
International Preliminary Report on Patentability received in PCT/JP2016/060261 dated Oct. 12, 2017.
International Search Report received in PCT/JP2016/060261 dated Jun. 21, 2016.
Molina-Bolivar et al. (Journal of Macromolecular Science Part C,Polymer Reviews, 45:59-98, 2005).
Office Action received in European Patent Application No. 16772896.3 dated Nov. 8, 2019.
Partial Supplementary European Search Report issued in corresponding European Patent Application No. 16772896.3 dated Jul. 13, 2018.
Topper, M.J., et al., Enzyme-Linked Immunosorbent Assay for Thrombin-Antithrombin III Complexes in Horses, American Journal of Veterinary Resea 57(4):427-431, 1996.

*Primary Examiner* — Carmencita M Belei
(74) *Attorney, Agent, or Firm* — Knobbe, Martens, Olson & Bear, LLP

(57) ABSTRACT

A method for measuring TAT complexes in a sample separated from a living body includes measuring TAT by performing latex immunoagglutination reaction under a condition of pH 5.8 to 6.6 using a TAT assay reagent. The TAT assay reagent includes a first antibody bound to a first latex particle, which binds to the antithrombin part of the TAT complex and recognizes the complex, and a second antibody bound to a second latex particle, which binds to the thrombin part of the TAT complex and recognizes the complex.

3 Claims, 6 Drawing Sheets

REAGENT AND METHOD FOR ASSAYING THROMBIN-ANTITHROMBIN COMPLEX

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the invention

The present invention relates to a reagent and a method for assaying the thrombin (T)-antithrombin (AT) complex (TAT) in a biological sample.

Description of the Related Art

The thrombin-antithrombin complex (TAT) is a protein complex generated in blood in the course of blood coagulation and the quantification of TAT complexes in blood is useful for the diagnosis of thrombosis, such as disseminated intravascular coagulation (DIC). However, the abundance of TAT complex is approximately $1/100,000$ of the abundance of free antithrombin and, therefore, the measurement of TAT complex is not easy.

Examples of a currently prevailing TAT quantification method include reagent kits employing enzyme immunoassay (ELISA) technologies, such as Enzygnost® TAT micro from Siemens AG, and reagent kits employing chemiluminescent enzyme immunoassay (CLEIA) technologies, such as STACIA® CLEIA TAT from LSI Medience Co. However, any of them are assay methods requiring separation between solid and liquid phases (B/F separation), which need laborious washing operations by hands or by special machines.

Patent Documents 1-3 and 5 have reported reagent systems for the TAT assay based on latex agglutination assay, any of which aims to assay samples prepared by diluting TAT complexes synthesized ex vivo with a buffer solution. However, there is no report on any reagent that enables the precise concentration of TAT complexes in human samples to be measured using latex agglutination assay. Moreover, in any of the methods described in these documents, the effect of the cross-reactivity of an antibody used is circumvented by establishing a TAT assay reagent based on the specificity thereof or by adding an additive agent. Patent Document 4 discloses an assay of TAT by a sandwich method using an antibody with no cross-reactivity but the assay lacks sufficient sensitivity for clinical use. Also, in any of the documents, it is not examined how much the pH during the measurement reaction influences on the measurement results when TAT complexes in samples are quantified. There has been no attempt so far to allow the reaction to proceed at an acidic pH in the TAT assay by latex immunoagglutination assay.

Accordingly, there has been a need for a reagent and a method for assaying TAT complexes in a biological sample with high sensitivity and high accuracy based on latex agglutination assay, which is characterized by simplified measurement operations.

PRIOR ART DOCUMENTS

Patent Documents

Patent Document 1: Japanese Unexamined Patent Publication No. 2001-289850
Patent Document 2: Japanese Unexamined Patent Publication No. Hei7-238099
Patent Document 3: Japanese Unexamined Patent Publication No. 2002-316999
Patent Document 4: Japanese Unexamined Patent Publication No. Hei3-48158
Patent Document 5: Japanese Unexamined Patent Publication No. 2001-228153

SUMMARY OF THE INVENTION

Problems to be Solved by the Invention

An object of the present invention is to provide a reagent and a method for assaying TAT complexes in a biological sample based on latex agglutination assay, which does not essentially require B/F separation and washing operations, and to provide a method for selecting an antibody for use in the assay.

The TAT assay has been considered to be clinically useful in respect of improving the sensitivity and the specificity of the diagnostic criteria for DIC or in respect of the availability of the measurement as a diagnosis by exclusion, in which DIC is seen to be negative where the measured TAT value is normal. However, the fact that ELISA, which needs laborious operations, and CLEIA, which requires a special machine, are currently prevailing TAT assay methods is likely a reason for the slow spread of the assay.

Accordingly, there has been a need for a reagent and a method for assaying TAT complexes in a biological sample with high sensitivity and high accuracy based on latex agglutination assay, which is characterized by simplified measurement operations.

Moreover, in consideration of the clinical significance of the assay, it requires a detection sensitivity allowing measurements of nanogram amounts as seen in CLEIA; however, it is a very challenging task to achieve the same level of sensitivity in latex agglutination assay as that in CLEIA, based on its measurement principle including the properties of particles used and the like.

Also, since, unlike ELISA, CLEIA, and the like, latex agglutination assay does not comprise the step of B/F separation by washing and the like, it is an objective in the establishment of a reagent and an assay method to overcome the cross-reactivity to substances other than the original target of interest, such as free antithrombin and the like.

Means for Solving the Problems

The inventors studied intensively to solve the above-described problems. Consequently, the inventors found that in an assay of TAT complexes in a biological sample based on latex agglutination assay, a TAT assay reagent with high sensitivity and high accuracy was successfully produced by using an antibody with cross-reactivity and utilizing the difference in cross-reactivity of the antibody. That is, the inventors found that TAT complexes in a biological sample were successfully measured accurately while minimizing the influence of free antithrombin by using an antibody, as one of the antibodies, selected by indirect inhibition ELISA and having a reactivity to TAT that is 100 or more times higher than the reactivity to free antithrombin. Furthermore, the inventor found that in the assay of TAT complexes in a biological sample based on latex immunoagglutination assay, TAT complexes in a biological sample were successfully measured sensitively and specifically by allowing the agglutination reaction to proceed under weak acidic conditions, and thereby completed the present invention.

That is, the present invention will provide the following items.

[1] A thrombin-antithrombin complex (TAT) assay reagent, the TAT assay reagent comprising:
an antibody bound to a latex particle which binds to the antithrombin part of the TAT complex and recognizes the complex; and
an antibody bound to a latex particle which binds to the thrombin part of the TAT complex and recognizes the complex;
wherein the antibody binding to the antithrombin part of the TAT complex and
recognizing the complex has a reactivity to TAT that is 100 or more times higher than the reactivity to free antithrombin.

[2] The TAT assay reagent according to [1], wherein the assay reagent is designed to achieve a pH of 5.8 to 6.6 during the assay.

[3] The TAT assay reagent according to [1] or [2], comprising:
a second reagent comprising
   latex particles coupled to the antibody which binds to the antithrombin part of the TAT complex and recognizes the complex and
   latex particles coupled to the antibody which binds to the thrombin part of the TAT complex and recognizes the complex; and
a first reagent comprising a buffer solution at a pH of 5.8 to 6.6.

[4] A method for measuring TAT complexes in a sample separated from a living body, wherein TAT is measured by latex agglutination assay using the TAT assay reagent according to any one of [1] to [3].

[5] A method for screening an antibody for use in the TAT assay of a sample separated from a living body by latex agglutination assay, the method comprising: preparing candidate antibodies;
allowing the candidate antibodies to react with a certain amount of free antithrombin; subjecting the thus-obtained reaction liquids to an enzyme immunoassay using a TAT-immobilized substrate to quantify the reactivity of the antibodies to free antithrombin;
comparing the reactivity of the antibodies to free antithrombin with that to TAT; and selecting an antibody having a reactivity to TAT that is 100 or more times higher than the reactivity to free antithrombin.

[6] A thrombin-antithrombin complex (TAT) assay reagent, comprising:
a first antibody bound to a latex particle which binds to the antithrombin part of the TAT complex and recognizes the complex; and
a second antibody bound to a latex particle which binds to the thrombin part of the TAT complex and recognizes the complex;
wherein the assay reagent is designed to achieve a pH of 5.8 to 6.6 during the assay.

[7] The TAT assay reagent according to [6], comprising:
a second reagent comprising
   latex particles coupled to the first antibody and
   latex particles coupled to the second antibody; and
a first reagent comprising a buffer solution at a pH of 5.8 to 6.6.

[8] A method for measuring TAT complexes in a sample separated from a living body, comprising measuring TAT by performing latex immunoagglutination reaction under a condition of pH 5.8 to 6.6 using the TAT assay reagent according to [6] or [7].

Advantageous Effect of the Invention

Conventionally, to empirically find out the best combination of antibodies was a commonly used technique in the selection of antibodies for use in immunological assay methods. That is, as many combinations of antibodies as possible are examined and a combination of antibodies providing excellent results in fidelity, sensitivity and specificity is selected for an assay method. However, random combination of several types of antibodies cannot always establish any reagent and/or measuring system with desired properties concerning sensitivity and specificity but may rather be entirely ineffective. Thus, in many cases the establishment of immunological assay methods has been heavily dependent on the specificity of antibodies and, therefore, even those skilled in the art have often been required to bear excessive burdens. Consequently, it has been difficult to produce any reagent or to establish any measuring system with high fidelity, sensitivity and specificity.

According to one embodiment of the present invention, the above-described problems can be solved. That is, antibodies available for latex agglutination assay can be efficiently selected and, thus, a reagent excellent in fidelity, sensitivity and specificity can be timely marketed.

Moreover, the reagent for latex agglutination assay provided in the present invention can accurately measure (quantify) a tiny amount of TAT in a biological sample while circumventing the effect of background substances such as plasma matrices. Also, it is an advantage of the reagent that the reagent allows the measurement on a general-purpose auto-analyzer and eliminates limitations, such as manual operation steps and measurement on a special machine.

According to one embodiment of the present invention, it is possible to prepare a reagent providing both excellent sensitivity and specificity by keeping the pH during the reaction in the weak acidic range. It was found that the increase in pH tended to decrease in the saline blank value, the plasma blank value and the reactivity to TAT in a pH-dependent manner. It was a surprising phenomenon found by the inventors that the reactivity was decreased at a pH higher than neutral. Thus, it is now possible to provide a reagent having high reactivity and high specificity by keeping the pH during the reaction in the weak acidic range.

DETAILED DESCRIPTION OF THE PREFERRED EMBODIMENT

Figure 1:
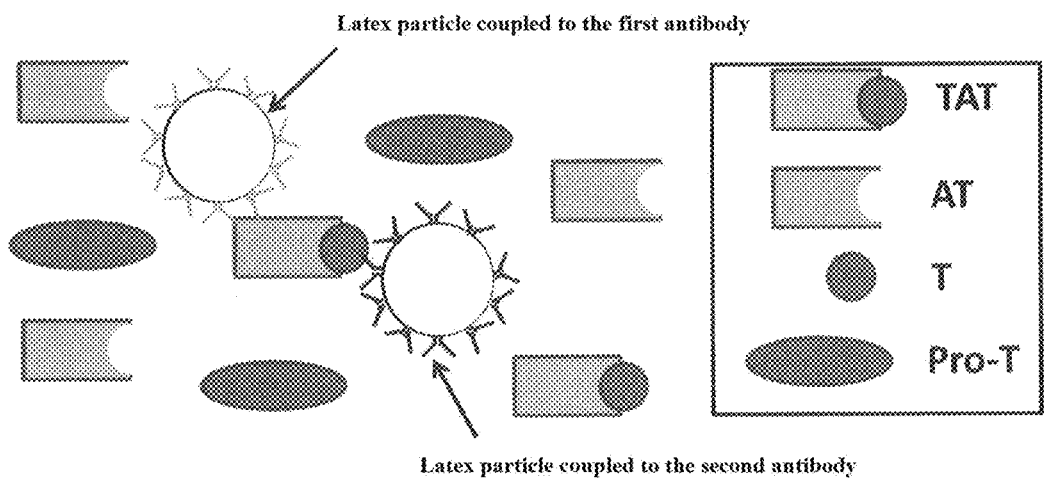
FIG. 1 shows a schematic diagram of the TAT assay method based on latex agglutination assay.

Herein after, an example of a TAT assay reagent is described as one embodiment, which is composed of an antibody binding to the antithrombin part of the TAT complex and recognizing the complex as a first antibody and an antibody binding to the thrombin part of the TAT complex and recognizing the complex as a second antibody, but the scope of the present invention will not be limited thereto.

For example, the TAT assay reagent of the present invention is a reagent for an immunoassay to measure TAT complexes in a biological sample by latex agglutination assay in a sandwich system using latex particles coupled to either of two different antibodies against TAT.

The first antibody is not limited as long as it is an anti-TAT antibody which binds to the antithrombin part of the TAT complex and recognizes the complex, but it is preferable to use an anti-TAT antibody having a low level of cross-reactivity to free antithrombin because the abundance of TAT complexes in blood is very low relative to that of free antithrombin.

Specifically, the TAT assay reagent of the present invention is preferably a TAT assay reagent comprising a first antibody bound to a latex particle which binds to the antithrombin part of the TAT complex and recognizes the complex, and a second antibody bound to a latex particle which binds to the thrombin part of the TAT complex and recognizes the complex, wherein the first antibody has a reactivity to TAT that is 100 or more times higher than the reactivity to free antithrombin. For the antibodies bound to latex particles, the two different antibodies may be coupled to two different types of particles, respectively, or the plural types of antibodies may be coupled to one type of particle, or either one of the antibodies may be coupled to several types of particles and then mixed for use.

As demonstrated in the Examples below, it was a surprising result that a sufficient effect was achieved by a first antibody which had a reactivity to TAT that was at least 100 times higher than the reactivity to free antithrombin. That is, the reactivity of the first antibody to TAT may be 100 or more times higher than the reactivity to free antithrombin and is preferably 1,000 or more times higher and more preferably 10,000 or more times higher than the reactivity to free antithrombin. The maximum extent of cross-reactivity is not particularly specified because a lower level of cross-reactivity is better, but the cross-reactivity to free antithrombin may be, for example, 100,000 times or 50,000 times less than the reactivity to TAT.

In the preparation of the above-described first antibody, either free antithrombin or TAT may be used for the immunization in animals other than human and the resulting antibody may be used in the present invention as long as it can bind to the antithrombin part of the TAT complex and recognize the complex.

As used in the present invention, the phrase "binding to the antithrombin part" means binding to antithrombin in a complex (TAT) formed by the association of free antithrombin, which is most abundant in a sample, with free thrombin. Accordingly, in cases where the antithrombin in a conformation achieved when it forms the complex is referred to as antithrombin in the complex-form structure and the antithrombin in a conformation achieved when it does not form the complex is referred to as antithrombin in the free-form structure (free antithrombin), the phrase "binding to the antithrombin part" means binding to the antithrombin in the complex-form structure.

The antithrombin in the free-form structure has a conformation different from that of the antithrombin in the complex-form structure. The reason is that the antithrombin in the free-form structure changes its conformation through the formation of a complex associated with free thrombin and maintains the changed conformation.

The second antibody is not limited as long as it is an antibody which can bind to the thrombin part of the TAT complex and recognize the complex, but an antibody which specifically reacts with thrombin can be used. Even an antibody which has cross-reactivity to free thrombin may often be used because free thrombin molecules are quite rare in a sample. Those skilled in the art will be able to select and use appropriate antibodies.

In the preparation of the above-described antibody, either free thrombin or TAT may be used for the immunization in animals other than human and the resulting antibody may be used in the present invention as long as it can bind to the thrombin part of the TAT complex and recognize the complex.

As used in the present invention, the phrase "binding to the thrombin part" means binding to thrombin in a complex (TAT) formed by the association of free thrombin, which is present in a sample, with antithrombin. Accordingly, in cases where the thrombin in a conformation achieved when it forms the complex is referred to as thrombin in the complex-form structure and the thrombin in a conformation achieved when it does not form the complex is referred to as thrombin in the free-form structure, the phrase "binding to the thrombin part" means binding to the thrombin in the complex-form structure.

It is possible that the thrombin in the free-form structure has a conformation different from that of the thrombin in the complex-form structure. The reason is that the thrombin in the free-form structure changes its conformation through the formation of a complex associated with antithrombin and maintains the changed conformation.

Either polyclonal or monoclonal antibodies may be used for the above-described first and second antibodies. Those skilled in the art will be able to obtain these antibodies according to known procedures.

Animals such as sheep, horse, goat, rabbit, mouse, rat, and the like may be used as animals to be immunized with an immunogen for the preparation of an antibody, and rabbit, goat, and the like are preferably used especially for the preparation of polyclonal antibodies. Moreover, monoclonal antibodies can be obtained by known methods to prepare hybridoma cells, and mouse, rat, rabbit or the like is preferably used in that case.

TAT may be used as an immunogen, as described above. Alternatively, an antibody produced by using a complex associated with vitronectin, VTAT, as an immunogen can also be used in the present invention. Moreover, antithrombin and thrombin may be used for the first and second antibodies, respectively.

For these immunogens, TAT complexes purified from a raw material, that is, a sample collected from a living body or TAT complexes synthesized in vitro by combining free thrombin and free antithrombin molecules may be used. The synthetic TAT complexes may be, for example, TAT complexes obtained by incubating in vitro thrombin and antithrombin molecules available as biologics, while TAT complexes expressed using a known translation system such as those in *E. coli,* mammalian cells, insect cells infected with baculovirus, and the like may be recovered, purified and used as an immunogen.

Moreover, in cases where immunity to recognize a difference in conformation can be induced with a partial peptide alone, specifically, in cases where it is desired in the production of an antibody to specify the binding site of the antibody, partial peptides of antithrombin and thrombin may be used for the production of the first and second antibodies, respectively. In that case, as a method of selecting a peptide sequence for an antigen, a method of synthesizing a peptide fragment, and an immunization method, known methods can be used.

The assay method based on latex agglutination assay will be described by reference to FIG. 1. As shown in FIG. 1, when the first antibody binds to the antithrombin part of the TAT complex and the second antibody binds to the thrombin part of the TAT complex, agglutination of the latex particles occurs and allows the determination of the TAT concentration based on the absorbance measured at that time.

The ratio of TAT to free antithrombin which fails to form TAT both present in a living body is considered to range from 1:60,000 to 1:110,000 on the basis of the range measured in normal subjects and generally considered to be approximately 1:100,000. Moreover, although it is known that the ratio may be changed in patients with sepsis and/or hepatic diseases, the ratio is considered to be around 1:50,000 even in cases where the amount of free antithrombin is relatively low. Thus, if the first antibody also has reactivity to free antithrombin, the quantification of TAT will become difficult. Then, an antibody having a low level of reactivity to free antithrombin should be used for the quantification of TAT. Although it is considered that the reactivity of the antibody to TAT should be 50,000 to 100,000 or more times higher than the reactivity to free antithrombin on the calculation basis, it was found in the present invention as demonstrated in the Examples below that the quantification of TAT is fully possible by using an antibody as the first antibody where the antibody has a reactivity to TAT that is 100 or more times higher than the reactivity to free antithrombin.

As used in the present invention, the phrase "a reactivity to TAT that is 100 or more times higher than the reactivity to free antithrombin" refers to a case where the ratio of the affinities for individual antigens (TAT and free antithrombin) is 100 or more, a case where the ratio of the amounts of antigens required to exhibit a certain inhibition rate in measurement by means of indirect inhibition ELISA described below is 100 or more, and the like.

The case where an antibody having a reactivity to TAT that is 100 or more times higher than the reactivity to free antithrombin is examined or screened by indirect inhibition ELISA will be described.

At first, an antibody binding to the antithrombin part of the TAT complex and recognizing the complex (a candidate antibody for the first antibody) is prepared. Such an antibody as an antibody directed against a binding site on the antithrombin part of the TAT complex and recognizing the complex may be selected from antibodies obtained in advance by a method, such as the method described below to prepare monoclonal antibodies by hybridoma cells. Of course, a previously known antibody directed against a binding site on the antithrombin part of the TAT complex and recognizing the complex would likewise be used in the assessment system below.

That is, a candidate antibody is allowed to react with a solution containing TAT or an antigen capable of inhibiting the reaction with TAT in a certain amount (for example, 0.1, 0.5, 1, 5, 10, 50 µg/mL) for a sufficient period of time (for example, 12 hours). Then, the reaction liquid is allowed to react with a TAT-immobilized substrate for a certain period of time. Subsequently, after washing, a labeled secondary antibody is used to measure the amount of the antibody bound to the TAT on the substrate (the percentage of residual antibody).

For example, at first, a certain amount of TAT complexes are immobilized onto a substrate, such as a plate, under a condition where any antigen that inhibits the reaction with the corresponding antibody is not present. Those skilled in the art will be able to appropriately determine the amount of the antigen (TAT) immobilized onto a substrate in view of the relationships between the quantity of the used antigen and the type of the assessed antibody.

The above-described candidate antibody for the first antibody in each concentration (for example, 0.04 to 1 µg/mL) is allowed to react with the above-described TAT-immobilized substrate for a certain period of time under a condition where any antigen that inhibits the reaction with the corresponding antibody is not present. Subsequently, after washing, a labeled secondary antibody (anti-mouse IgG-HRP) is used to measure the amount of the antibody bound to the TAT on the substrate. The concentration of the antibody which gives an absorbance of around 1.0 (corresponding to 1000 according to the method described in Table 1) is determined. This antibody concentration can be considered to be a concentration of the antibody in the inhibition with the antigen (Table 3; concentration during the reaction [µg/mL]).

Next, the candidate antibody in a concentration determined by the above-described method is allowed to react with a solution containing TAT or free antithrombin in a certain amount (for example, 0.1, 0.5, 1, 5, 10, 50 µg/mL) for a sufficient period of time (for example, 12 hours). Then, the reaction liquid is allowed to react with a TAT-immobilized substrate for a certain period of time. Subsequently, after washing, a labeled secondary antibody (anti-mouse IgG-HRP) is used to measure the amount of the antibody bound to the TAT on the substrate (the percentage of residual antibody).

Additionally, the percentage of residual antibody can be calculated relative to the detection value obtained for the case where absorption with antigen is not performed, which is considered as 100%.

In cases where the reactivity of the antibody to free antithrombin is high, the antibody capable of binding to TAT is decreased in amount and thus the antibody detected by the labeled secondary antibody is decreased in amount (the percentage of residual antibody is decreased), while in cases where the reactivity of the antibody to free antithrombin is low, a more amount of the antibody remains capable of binding to TAT and thus the antibody detected by the labeled secondary antibody is increased in amount (the percentage of residual antibody is increased).

This percentage of residual antibody will be compared with a percentage of residual antibody obtained when the antibody is first reacted with TAT (the inhibition reaction is performed with TAT) and then the reaction liquid is reacted with the immobilized TAT.

Next, in cases where, for example, a percentage of residual antibody of 50% is obtained in the inhibition reaction by adding free antithrombin to a concentration of 50 µg/mL, the amount of TAT required to achieve the same percentage of residual antibody is calculated based on the above-described result from the inhibition with TAT. In cases where the amount of the TAT inhibitory antigen required to achieve a percentage of residual antibody of 50% is less than 0.50 µg/mL when the inhibition is performed with TAT, the reactivity to TAT can be considered to be 100 or more times higher than the reactivity to free antithrombin.

The thus selected antibody can be selected as a first antibody. Additionally, in cases where the first antibody is a monoclonal antibody, its affinity (Kd) for TAT is preferably equal to or less than $10^{-8}$. However, those skilled in the art will be able to appropriately select an antibody suitable for a latex reagent based on the affinity value for TAT.

Examples of the antibody used in the present invention include antibody fragments. The antibody fragments are fragments of a desired antibody, which moreover have the same reactivity as that of the original antibody. Examples of an antibody fragment that can be used in the present invention include fragments such as Fab, Fab', F(ab')$_2$, or Fv. Any of these fragments can be obtained, for example, by digestion of an antibody with a protein degradation enzyme according to a conventional method, followed by separation and purification according to conventional methods for protein separation and purification. These fragments may be directly immobilized onto latex particles and used, while fragments may be prepared as Fab' or F(ab')$_2$ fragments and immobilized onto latex particles. Fab' and F(ab')$_2$ fragments are more preferable in consideration of avoiding a non-specific reaction of an antibody to Fc fragments.

An antibody used in the present invention can be obtained by first producing anti-TAT antibodies (candidate antibodies) by a production method for monoclonal antibodies with hybridoma cells, and the like, and then selecting an antibody which shows a low level of cross-reactivity to free antithrombin, specifically an antibody having a reactivity to TAT that is 100 or more times higher than the reactivity to free antithrombin, from the anti-TAT antibodies (candidate antibodies) according to the procedures and criteria as described above.

The candidate antibodies can be obtained, for example, by a production method for monoclonal antibodies with hybridoma cells produced by a known cell fusion method. Antibody-producing cells may be selected from animals except for human, for example, mouse, rat, guinea pig, and the like. Hybridoma cells and monoclonal antibodies can be prepared according to conventional methods, for example, methods described in "Zoku-Seikagaku Jikken Koza" (Biochemical Experiment Training Course; The Japanese Biochemical Society, ed.) or "Men-eki Seikagaku Kenkyu-hou" (Immuno-biochemical research methods; The Japanese Biochemical Society, ed.).

The second antibody is not particularly limited as long as it is an antibody which binds to the thrombin part of the TAT complex and recognizes the complex. In cases where it is a monoclonal antibody, its affinity (Kd) for TAT is preferably equal to or less than $10^{-8}$. However, those skilled in the art will be able to appropriately select an antibody suitable for a latex reagent based on the affinity value for TAT. For the method to select the antibody, antibodies produced similarly to the first antibody can be used.

The combination of the first antibody and the second antibody is not particularly limited as long as it allows the assay of TAT by latex agglutination assay, but a combination of the antibodies which is minimally affected by the matrices contained in a biological sample such as plasma (background) is preferably selected.

The sensitivity required for the TAT assay reagent should be sufficient to measure the reference value with which normal subjects can be clearly distinguished from patients, or a concentration 2-fold higher than the reference value and, therefore, the reagent of the present invention is preferably a reagent capable of quantifying TAT complexes at a concentration of 10 to 15 ng/mL, more preferably a reagent capable of quantifying TAT complexes at a concentration of 3 to 4 ng/mL, and further preferably a reagent capable of quantifying TAT complexes even at a concentration of around 1 ng/mL, in a biological sample.

The latex particles to which the above-described first and second antibodies are coupled are not particularly limited as long as they can be used in the latex agglutination reaction, but they have an average particle size of preferably 0.05 µm to 0.5 µm and more preferably 0.2 to 0.4 µm.

For the latex particles to be used, only one type of latex particle or multiple types of latex particles may be used. For example, a combination of latex particles with different particle sizes may be used. Because it is practically difficult to manufacture latex particles with a single particle size, any latex particle is specified with the average particle size of all particles. Accordingly, in the reference to an average particle size of 0.05 µm to 0.5 µm, a case comprising latex particles outside this range may also be included in the present invention. The fact that latex particles with different particle sizes are included in a given latex particle is within the common sense of those skilled in the art and those skilled in the art will be able to establish a latex reagent by using a solution containing a group of particles having a not highly heterogeneous size distribution.

Additionally, the average particle size can be measured according to a known method and, for example, can be calculated on the basis of image analysis using a transmission electron microscope system.

The latex particle according to the present invention is not particularly limited as long as it is commonly used in the art, but examples of the latex particle include particles made from homopolymers (for example, polystyrene, methacrylate polymers, acrylate polymers, and the like) composed of polymerized vinyl monomers such as styrene, vinyl chloride, acrylonitrile, vinyl acetate, acrylate, methacrylate, and the like; particles made from butadiene copolymers (for example, styrene-butadiene copolymer, methylmethacrylate-butadiene copolymer, acrylonitrile-butadiene copolymer, and the like); and particles made from other copolymers (for example, styrene-styrenesulfonate copolymer, methacrylate copolymers, acrylate copolymers, vinyl chloride-acrylate copolymers, and the like). Examples of the latex particle include particles carrying a carboxyl group, a primary amino group, a carbamoyl group (—CONH$_2$), a hydroxyl group, an aldehyde group, or the like as a functional group and having a base body composed of any of the above-described organic particulates.

For the method to immobilize the antibodies onto latex particles, the antibodies may be immobilized according to a known method and can be immobilized by treatments commonly used in the art, such as, for example, suspending the antibody and latex particles in a buffer solution, allowing them to react at 25° C. for one hour, followed by centrifugation, blocking treatment, and the like. Moreover, a method to immobilize the antibodies onto latex particles through chemical linkage or through biotin-avidin interaction may be selected.

The coupling of the antibodies to latex particles is performed under conditions where the antibodies can maintain the above-described reactivity and specificity to TAT.

For ease of preparation of preferable reagents, an antibody-immobilized latex liquid may be prepared for every antibody as a first latex particle and a second latex particle onto which the first antibody and the second antibody have been immobilized, respectively, while the reagents may be prepared by immobilizing the first antibody and the second antibody onto a single type of latex particles. Those skilled in the art will be able to appropriately design how to immobilize the antibodies onto latex particles and to prepare reagents.

The reagent of the present invention may be a single-reagent system or a two-reagent system. If the reagent of the present invention is a single-reagent system, TAT complexes in a biological sample can be measured by adding a suspension of latex particles carrying the immobilized antibodies to the biological sample, and causing an antigen-antibody reaction. If the reagent of the present invention is a two-reagent system, TAT complexes in a biological sample can be measured by adding the first reagent mainly composed of buffer ingredients to the biological sample and then further adding the second reagent containing latex particles onto which the antibodies have been immobilized, and causing an antigen-antibody reaction.

The degree of agglutination of latex particles can be measured, for example, using absorbance, while the concentration of TAT complexes in a sample can be quantified by searching for a concentration corresponding to the degree of agglutination on a previously obtained standard curve of the reference. Additionally, the measurement of absorbance may be performed at a measurement wavelength of normally 340 nm to 1000 nm and preferably 500 nm to 900 nm. When the latex agglutination reaction is analyzed by photometry, the kinetics of agglutination or the variation in agglutination over a fixed time interval during the proceeding of the latex agglutination reaction can be determined by photometry. For example, when the measurement of absorbance is performed, the kinetics of absorbance changes or the variation in absorbance over a fixed time interval within the period from 30 seconds to 5 minutes after the start of the latex agglutination reaction can be determined by photometry. The reaction temperature is preferably from 10 to 50° C. and more preferably from 20 to 40° C. The reaction time can be appropriately determined and the measurement may be performed, for example, within a reaction time of 10 to 15 minutes on a general-purpose auto-analyzer. Additionally, those skilled in the art will be able to appropriately determine the reaction temperature, the reaction time, the measurement wavelength, the measurement time, the reagent composition, the latex concentration, the concentration of an antibody to be immobilized onto latex particles, and the concentrations of various additive agents in analysis using an optical instrument or a general-purpose auto-analyzer.

The concentration of latex particles used in the present invention is not particularly limited as long as it is a concentration applicable to a reagent for an immunological assay based on latex agglutination assay, but the concentration of latex particles during the reaction required for the TAT assay is preferably 0.005% (w/v) to 0.2% (w/v) and more preferably 0.01% (w/v) to 0.1% (w/v).

The test sample applicable to the reagent of the present invention is not particularly limited as long as it is a test sample potentially containing TAT complexes, but it is preferably a biological sample. Examples of the biological sample may include cultured cells but also those preferably used in the measurement with serum or plasma. The biological sample is preferably a sample derived from any mammalian animal and more preferably a sample derived from human.

The reagent of the present invention may further comprise, in addition to the latex particles onto which the antibodies have been immobilized, excipients which can be added to a reagent for an immunological assay based on latex agglutination assay, such as, for example, a buffer, an agglutination promoter, a non-specific binding suppressor, a sensitizing agent, and the like. Examples of the sensitizing agent which can be added to the reagent of the present invention include sodium alginate, propylene glycol alginate, and the like. Moreover, a water soluble polymer or protein is preferably used as an agglutination promoter which can be added to the reagent of the present invention. Examples of the agglutination promoter include water soluble polymers such as dextran and dextran sulfate, polyvinyl alcohol, polyethylene glycol, polyvinylpyrrolidone, and the like; albumins such as bovine serum albumin; and globulins such as γ-globulin.

Moreover, a third antibody may be added for use. For the use of a third antibody, an antibody having a different rate of reaction is preferably used as the third antibody in cases where, for example, the measurable range of the TAT assay reagent is desired to cover a broad range from a low concentration to a high concentration.

In respect of the above-described buffer, the buffer solution has a buffer capacity at a pH of preferably 5.8 to 6.6, more preferably 6.0 to 6.4, further preferably 6.1 to 6.3, particularly preferably 6.15 to 6.25 and most preferably about 6.2. In the case of a single-reagent system the pH of the reagent should be adjusted to 5.8 to 6.6, while in the case of a two-reagent system the reagents should be composed such that the pH reaches 5.8 to 6.6 when they are mixed. For example, in an aspect where the reagent system comprises a first reagent mainly composed of buffer ingredients and a second reagent containing latex particles onto which the antibodies have been immobilized, the pH of the first reagent is adjusted to 5.8 to 6.6 and the pH of the mixture reaches 5.8 to 6.6 when both the reagents are mixed.

The pH may be adjusted by a pH modifying agent and is preferably adjusted by a buffer solution. A buffer solution such as Tris buffer, Bis-Tris buffer, phosphate buffer, or Good's buffer is preferably used and the concentration of the buffer solution during the reaction is preferably 10 to 500 mmol/L and more preferably 20 to 200 mmol/L.

Additionally, in cases where the pH of a mixture obtained when a blood sample is mixed with the reagent is outside the range of 5.8 to 6.6, the pH may be adjusted additionally by a pH modifying agent and the like.

Examples of the non-specific binding suppressor which can be added to the reagent of the present invention include antibodies or receptors against substances responsible for a non-specific reaction; buffer solutions, such as Tris buffer, phosphate buffer, glycine buffer, borate buffer, citrate buffer, acetate buffer, or Good's buffer; chelating agents, such as EDTA, CyDTA, DTPA, EGTA, NTA, and NTP; salts, such as sodium chloride, potassium chloride, sodium sulfate, calcium sulfate, magnesium sulfate, calcium carbonate, and sodium carbonate; and non-ionic surfactants, such as fatty acid diethanolamides, polyoxyethylene alkyl ethers, polyoxyethylene alkylphenyl ethers, fatty acid sorbitan esters, alkyl polygulcosides, alkyl monoglyceryl ethers, polyoxyethylene sorbitan fatty acid esters, fatty acid alkanolamides, and alkyl glycosides.

The reagent of the present invention may include TAT complexes which can be used as a standard substance. The TAT complexes may be TAT complexes purified from a living body or synthesized by recombinant DNA technology and the like. The synthetic TAT complexes can be obtained, for example, by incubating in vitro thrombin and antithrombin molecules available as biologics. Moreover, TAT complexes can also be synthesized by recovering and purifying and mixing the components which have been expressed using a known translation system in E. coli, mammalian cells, insect cells infected with baculovirus, and the like.

EXAMPLES

Example 1

Preparation of Synthetic TAT Complexes

A commercially available human thrombin formulation (manufactured by Japan Blood Products Organization) and a commercially available antithrombin formulation (manufactured by Japan Blood Products Organization) were separately diluted with PBS (produced by dissolving Dulbecco's PBS (−) powder "Nissui (manufactured by Nissui Pharmaceutical Co., Ltd.)" to a concentration of 9.6 g/L) and those dilutions were mixed at a molar ratio of 1:3 and then allowed to react at 37° C. for 30 minutes. After the 30 minutes, DFP (diisopropyl fluorophosphate, manufactured by Wako Pure Chemical Industries, Ltd.) was added to a concentration of 0.75 mM to stop the reaction.

Because unreacted thrombin and antithrombin were contained in the obtained reactant, purification was performed with a Hiload 26/60 Superdex 200 HR (manufactured by GE Healthcare) previously equilibrated with 50 mM Tris-HCl buffer (pH 7.4) containing 500 mM NaCl.

TAT fractions were recovered after identification by SDS-PAGE. The obtained TAT fraction was diluted with saline containing 0.5% BSA and analyzed using a CLEIA reagent (STACIA® CLEIA TAT, manufactured by LSI Medience Co.) to determine the concentration. The thus-obtained TAT complexes were used as synthetic TAT complexes.

Example 2

Preparation of an Anti-TAT Antibody

A cell fusion method was carried out according to the method described in Tamie Ando and Tatsuo Iwasaki, "Monoclonal Antibody/Hybridoma and ELISA" (Kodansha Ltd.).

The synthetic TAT complex prepared in Example 1 in an amount of 50 μg was mixed with Freund's complete adjuvant (manufactured by DIFCO) to provide an administered antigen.

The antigen was administered to BALB/c mice (female, four weeks old) three times at an interval of two weeks and 25 μg of the antigen, that is, half the amount of the original administered antigen was injected intravenously at the fourth administration.

One week later, lymphocytes were isolated from the spleen and mixed with P3×63-Ag.8 myeloma cells and then fused using polyethylene glycol (PEG 4000, manufactured by Merck).

Hybridoma cells were selected in HAT selection medium and then screened one week later for hybridoma clones producing an antibody of interest on the basis of the binding activity for the synthetic TAT complex. That is, the synthetic TAT complex was individually diluted with 0.05 M carbonate buffer (pH 9.5) to a concentration of 0.2 μg/mL and added at 50 μL/well to an immuno plate (Maxisorp, manufactured by NUNC). After the reaction at 4° C. overnight, each well was washed three times with PBS containing 0.05% Tween-20 and then blocked by adding thereto 100 μL of PBS containing 1.0% BSA.

Subsequently, the culture supernatant was added in a volume of 50 μL to each well and allowed to react at 37° C. for one hour and then each well was washed three times with PBS containing 0.05% Tween-20. A peroxidase-labeled anti-mouse immunoglobulin antibody (manufactured by Dako) was diluted 1000 times in PBS containing 0.05% Tween-20 and then added in a volume of 50 μL to each well.

After the reaction at 37° C. for one hour, each well was washed five times in a similar way and then a solution of o-phenylenediamine (manufactured by Wako Pure Chemical Industries, Ltd.) was added in a volume of 50 μL to each well. After the reaction at room temperature for 5 to 10 minutes, the reaction was stopped with 2 N sulfuric acid.

The absorbance was measured at 492 nm on a plate spectrophotometer (EL312e, manufactured by BioTek Instruments, Inc.). Cells producing antibodies showing good reactivity to the synthetic TAT complex were selected and then cloned by limiting dilution. Ten days later, those cells were further screened to obtain hybridoma clones producing antibodies which react with the synthetic TAT complex.

Example 3

Preparation of Anti-Thrombin Antibody

Anti-thrombin antibodies were obtained by a method similar to that in Example 2 using thrombin as an immunizing antigen. Antibodies specifically reacting with thrombin were selected and one of those clones was used as an anti-thrombin antibody (T-1).

Example 4

Evaluation of Antibody Specificity by Indirect Inhibition ELISA

Figure 2:
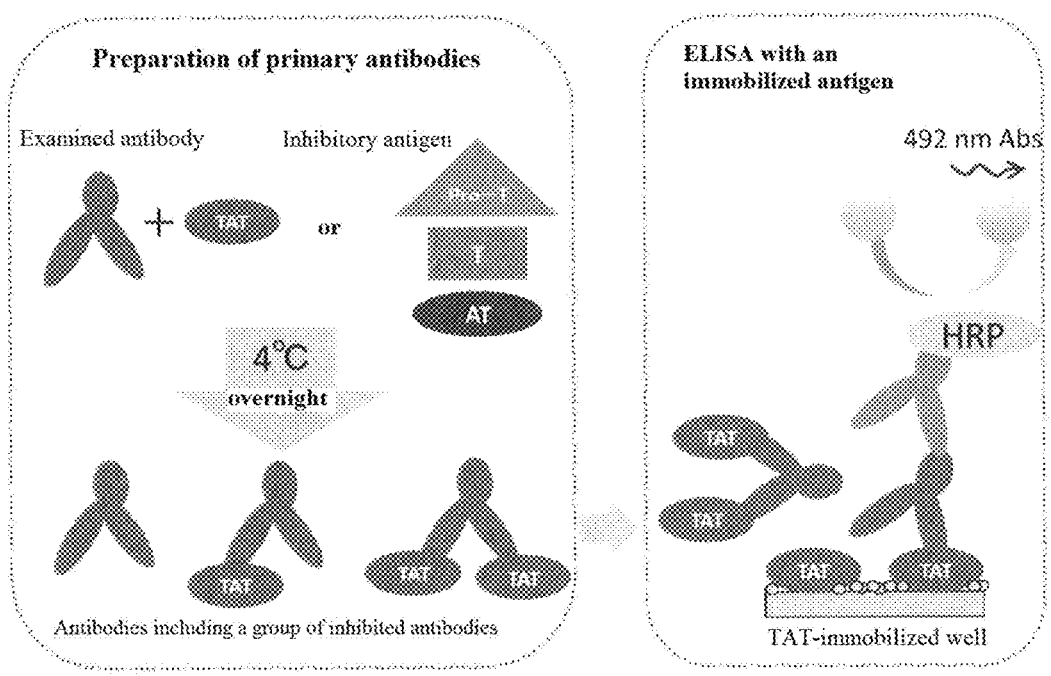
FIG. 2 shows a schematic diagram of the reaction system by indirect inhibition ELISA.

The reactivity of each antibody was evaluated by indirect inhibition ELISA. A schematic model of the reaction system by indirect inhibition ELISA is shown in FIG. 2.

Every TAT-recognizing antibody (anti-TAT antibody) candidate to be evaluated at a concentration of 0.04 to 0.4 μg/mL was mixed and incubated with each inhibitory antigen (prothrombin (manufactured by Enzyme Research Laboratories), thrombin, antithrombin, synthetic TAT complex). Those candidate antibodies, including a group of inhibited antibodies, were used as primary antibodies and allowed to bind to synthetic TAT complexes immobilized onto 96-well plates. Furthermore, a peroxidase-labeled anti-mouse immunoglobulin antibody (manufactured by Dako) was used as a secondary antibody and allowed to bind to the plates and then a chromogenic substrate was added to the plates to measure the absorbance. Moreover, the percentage of residual antibody in each candidate antibody was calculated based on the rate of color change.

For a particular antibody (TAT-5), the values of absorbance obtained when each inhibitory antigen was used were presented in Table 1, while the ratios of residual antibody calculated from the values of absorbance were presented in Table 2.

For example, if the concentration of the TAT inhibitory antigen is 10 μg/mL, the percentage of residual antibody will be 285/1066×100=26.7(%). The percentage of residual antibody in each antibody was calculated for each concentration of each antigen. Additionally, in the tables, Pro-T represents prothrombin, T represents thrombin, and AT represents antithrombin.

TABLE 1

Measurement results from indirect inhibition ELISA

| Inhibitory antigen | Pro-T | T | AT | TAT |
| --- | --- | --- | --- | --- |
| 0 | 1066 | 1066 | 1066 | 1066 |
| 0.016 | 1074 | 1059 | 1059 | 1063 |
| 0.08 | 1062 | 1062 | 1059 | 1045 |
| 0.4 | 1085 | 1067 | 1065 | 965 |
| 2 | 1064 | 1049 | 1033 | 661 |
| 10 | 1071 | 1057 | 1001 | 285 |
| 50 | 1072 | 1056 | 789 | 112 |

Inhibitory antigen concentration; μg/mL, Absorbance (492 nm×1000), N=2 for each measurement (average value)

TABLE 2

Percentage of residual antibody

| Inhibitory antigen | Pro-T | T | AT | TAT |
| --- | --- | --- | --- | --- |
| 0 | 100.0% | 100.0% | 100.0% | 100.0% |
| 0.016 | 100.8% | 99.3% | 99.3% | 99.7% |
| 0.08 | 99.6% | 99.6% | 99.3% | 98.1% |
| 0.4 | 101.8% | 100.1% | 99.9% | 90.5% |
| 2 | 99.8% | 98.4% | 96.9% | 62.0% |
| 10 | 100.5% | 99.2% | 93.9% | 26.7% |
| 50 | 100.6% | 99.1% | 74.0% | 10.5% |

Inhibitory antigen concentration; μg/mL

Moreover, the amount of the TAT antigen required to achieve an inhibition rate corresponding to the percentage of residual antibody obtained by inhibition with antithrombin at 50 μg/mL was calculated and compared with the amount of antithrombin to obtain the difference (fold increase) in the reactivity of each antibody to TAT relative to that to antithrombin. A larger difference in the reactivity of an antibody indicates the higher specificity of the antibody to TAT relative to that to antithrombin. Calculation was performed based on the TAT-inhibition curve (the logarithm of the concentration of the added inhibitory antigen versus the percentage of residual antibody) drawn with the spline function.

Figure 3:
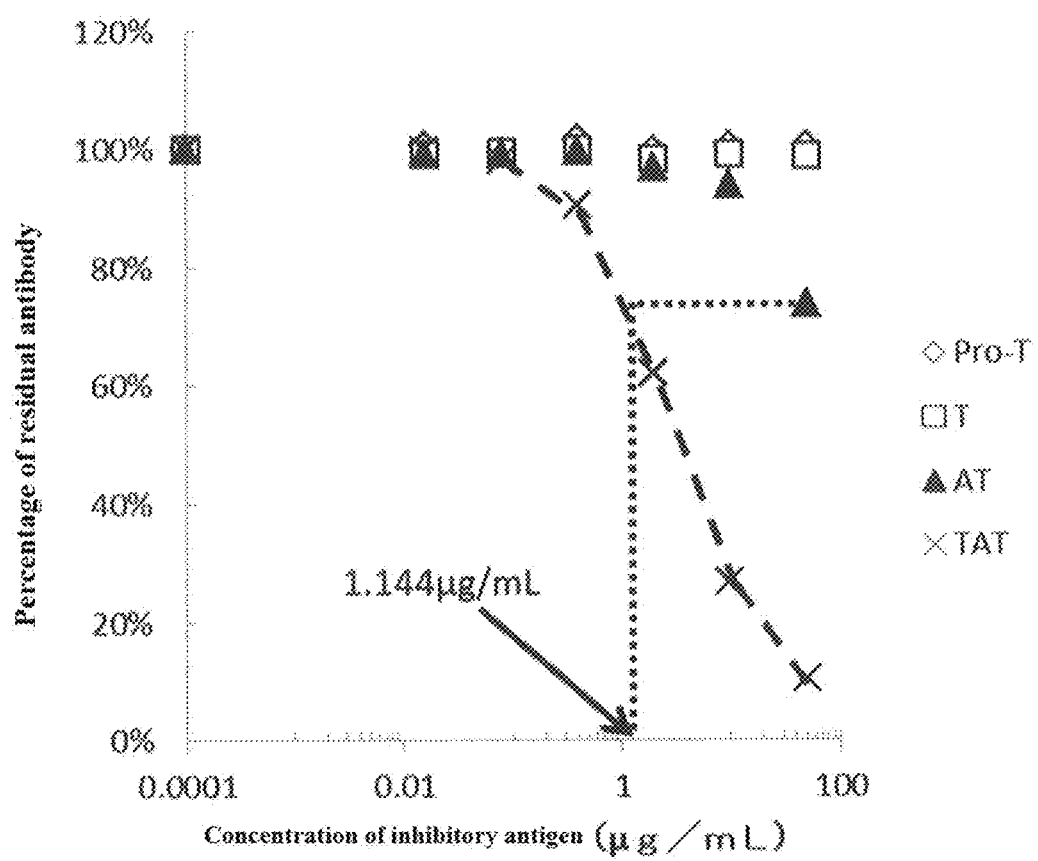
FIG. 3 shows the results from the evaluation of the reactivity of the clone TAT-5 to each indicated antigen in indirect inhibition ELISA.

For example, in the case of TAT-5, the percentage of residual antibody obtained with antithrombin at 50 μg/mL is 74.0%, while the amount of the TAT antigen required to achieve a percentage of residual antibody similar to that percentage is 1.144 μg/mL. That is, the difference in reactivity proves to be 50/1.144=44-fold (FIG. 3).

Furthermore, the above-described fold increase was calculated for 27 antibody clones. The difference (fold increase) in the amount of the added TAT complexes relative to that of the added antithrombin was 100 or more in thirteen among them, 1000 or more in seven among them, and 10000 or more in two among them. Five among those antibodies are presented in Table 3.

TABLE 3

| Clone | Concentration during the reaction (μg/ml) | Inhibition by AT at 50 μg/ml (percentage of residual antibody) | Amount of TAT required to achieve the same level of inhibition as that by AT at 50 μg/ml (μg/ml) | Fold increase (fold) |
| --- | --- | --- | --- | --- |
| TAT-1 | 0.04 | 88.2 | 0.001 | 49892 |
| TAT-2 | 0.08 | 92.3 | 0.029 | 1700 |
| TAT-3 | 0.08 | 89.4 | 0.230 | 218 |
| TAT-4 | 0.08 | 18.0 | 0.720 | 69 |
| TAT-5 | 0.40 | 74.0 | 1.144 | 44 |

Example 5

Evaluation of the Reactivity to TAT in Reagents for Latex Agglutination Assay

The antibodies against the antithrombin part evaluated by indirect inhibition ELISA in Example 4 (TAT-1, TAT-2, TAT-3, TAT-4, and TAT-5) and the antibody against the thrombin part obtained in Example 3 (T-1) were used in sensitization of latex particles and the resulting particles were used for the evaluation of reactivity.

Latex particles were sensitized with each antibody by allowing polystyrene latex particles with a size of 0.32 μm to adsorb the antibody, blocking them with 0.3% BSA solution, subsequently spinning down and washing them with a 0.05% solution of sodium azide (manufactured by Kishida Chemical Co., Ltd.), and then dispersing them again in a 0.05% solution of sodium azide.

Reagents containing the latex particles as produced above and sensitized with each antibody were prepared and used for the evaluation of reactivity to TAT. The compositions of the used reagents are as indicated below. For the first reagent, a composition of 100 mM Bis-Tris (manufactured by Dojindo Laboratories), pH 6.0, 500 mM NaCl, and 0.15% BSA was used. For the second reagent, particles sensitized with each antibody were diluted with 0.05% sodium azide to an absorbance of 1.0 at a wavelength of 700 nm and mixed for use.

Since a large amount of TAT complexes is contained in serum, serum was diluted with saline containing 0.5% BSA and analyzed with the CLEIA reagent to determine the concentration of TAT complexes and the dilution was used as the serum TAT fraction. The analyzed serum TAT fraction was diluted with pooled plasma (manufactured by Vitro-Logic) to a TAT concentration of 1000 ng/mL and the resulting dilution was used as a measurement sample.

The analyzer 7170S (manufactured by Hitachi High-Technologies Co.) was used as a measuring apparatus. Measurement parameters were set to 12 μL of sample volume, 90 μL of the first reagent, 90 μL of the second reagent, 570 nm of main wavelength, and 800 nm of subsidiary wavelength. The absorbance at the 34th photometric measurement point was subtracted by the absorbance at the 20th photometric measurement point and then multiplied by 10000 to determine ΔAbs and thereby the measurement was completed.

Figure 4:
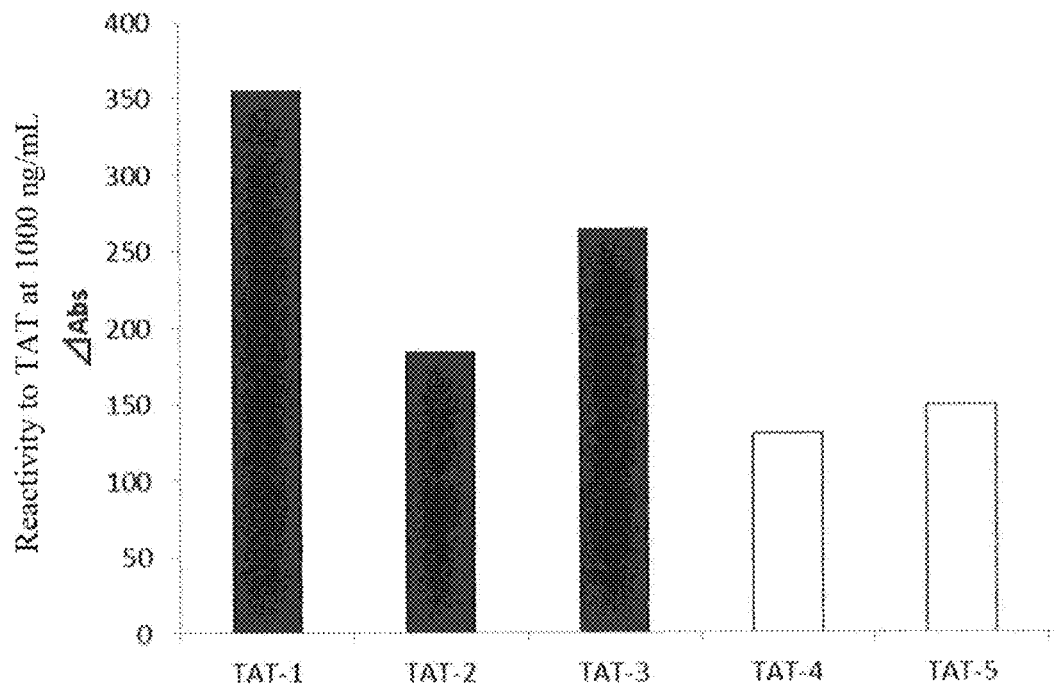
FIG. 4 shows the results from the evaluation of the reactivity of a latex reagent coupled to each indicated antibody against TAT.

The results are shown in FIG. 4. In any of the five antibodies shown in Table 3, the reactivity indicated by ΔAbs was 100 or more in the addition of TAT at 1000 ng/mL, in contrast to no addition of TAT.

In TAT-1, TAT-2 and TAT-3 shown in Table 3, the latex agglutination assay successfully confirmed the high reactivity of those antibodies. Moreover, also in the antibodies TAT-4 and TAT-5, a certain level of reactivity was confirmed, though lower than those of TAT-1, TAT-2 and TAT-3.

Example 6

Evaluation of the Cross-Reactivity to Antithrombin in Reagents for Latex Agglutination Assay The cross-reactivity to antithrombin in the prepared reagents was evaluated using samples prepared as described in Example 5 by diluting human serum with saline containing 0.5% BSA to a concentration of 1000 ng/mL and further supplemented with antithrombin to a concentration of 250 or 500 µg/mL.

The reactivity obtained when no antithrombin was added was compared with the reactivity obtained when antithrombin was added at each concentration.

To perform the measurement, any of the measuring reagents, measuring apparatus, and measurement parameters were similar to those in Example 4. The anti-TAT antibodies used for the evaluation are TAT-1, TAT-2, TAT-3, TAT-4 and TAT-5.

Figure 5:
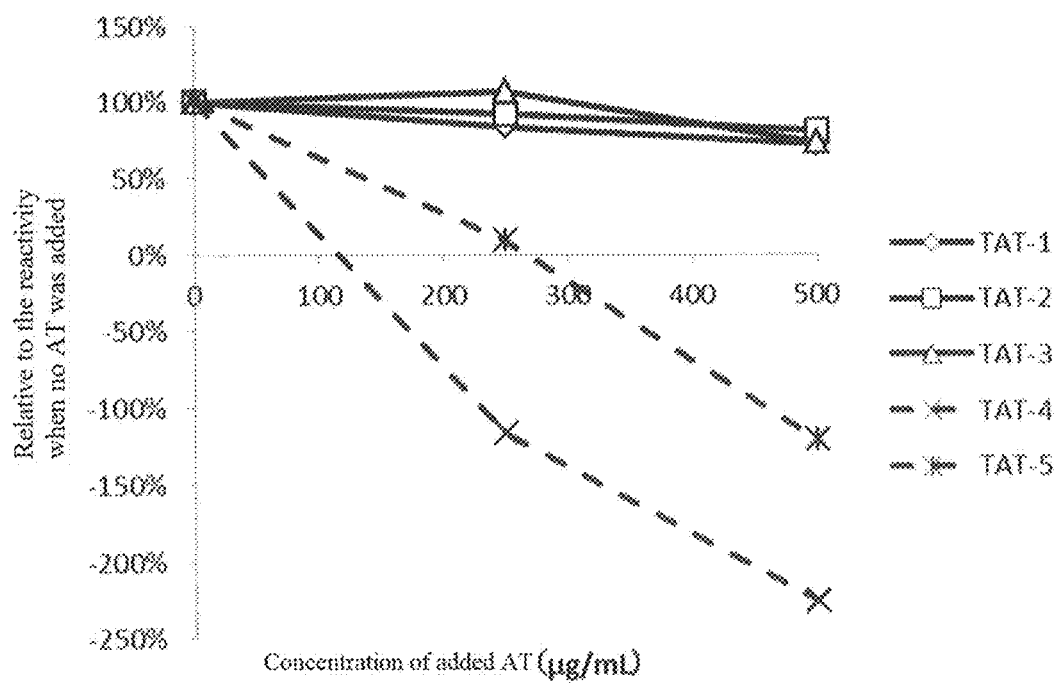
FIG. 5 shows the results from the evaluation of the cross-reactivity of a latex reagent coupled to each indicated antibody against free antithrombin.

The evaluation results of the cross-reactivity of the latex reagents to antithrombin are shown in FIG. 5. The antibodies that achieved a 100-fold or more specificity in the indirect inhibition ELISA of Example 4 (TAT-1, TAT-2, TAT-3) retained not less than 70% of the original reactivity even in the case of adding antithrombin to a concentration of 500 µg/mL. On the other hand, in either of the antibodies that achieved a 100-fold or less specificity (TAT-4, TAT-5), extreme reduction in reactivity due to the increased antithrombin concentration was observed (FIG. 5).

The cross-reactivity in each antibody whose reactivity had been confirmed in the latex agglutination reaction system of Example 5 was checked by ELISA and consequently it was indicated that while a high level of specificity was observed for each of the TAT-1, TAT-2 and TAT-3 antibodies in both the latex agglutination reaction systems, the specificity was insufficient in each of the TAT-4 and TAT-5 antibodies although a certain level of reactivity was observed for them in the latex agglutination assay.

Thus, it was confirmed that the antibodies which had been identified by the indirect inhibition ELISA of Example 4 to show a 100-fold or more difference in reactivity were very useful for use as reagents.

Example 7

Effect of the pH of the First Reagent

The effect of the pH of a latex reagent on reactivity was assessed by changing the pH from 5.7 to 7.2.

For the composition of the reagents, a composition of 100 mM Bis-Tris or MES (manufactured by Dojindo Laboratories), 700 mM NaCl, 0.15% BSA, 0.20% sodium alginate (manufactured by Wako Pure Chemical Industries, Ltd.), and 0.05% EMULGEN-150 (manufactured by Kao Co.) was used for a first reagent, while TAT-1 and T-1 were used as antibodies against the antithrombin part and the thrombin part, respectively, for a second reagent with diluting particles sensitized with each antibody in 0.05% sodium azide to an absorbance of 1.0 at a wavelength of 700 nm and mixing them. Sensitization of latex particles with each antibody was performed similarly to that in Example 5 except that particles with a particle size of 0.20 µm were used.

In the preparation of samples to be measured, saline containing 0.5% BSA (referred to as Saline) and human pooled plasma (referred to as Plasma) were used. Moreover, the human serum analyzed with the CLEIA reagent was diluted with the above-described pooled plasma to each concentration (10, 50, 100 ng/mL) and the resulting dilutions were used as TAT samples. To perform the measurement, the measuring apparatus and measurement parameters were similar to those in Example 4.

Figure 6:
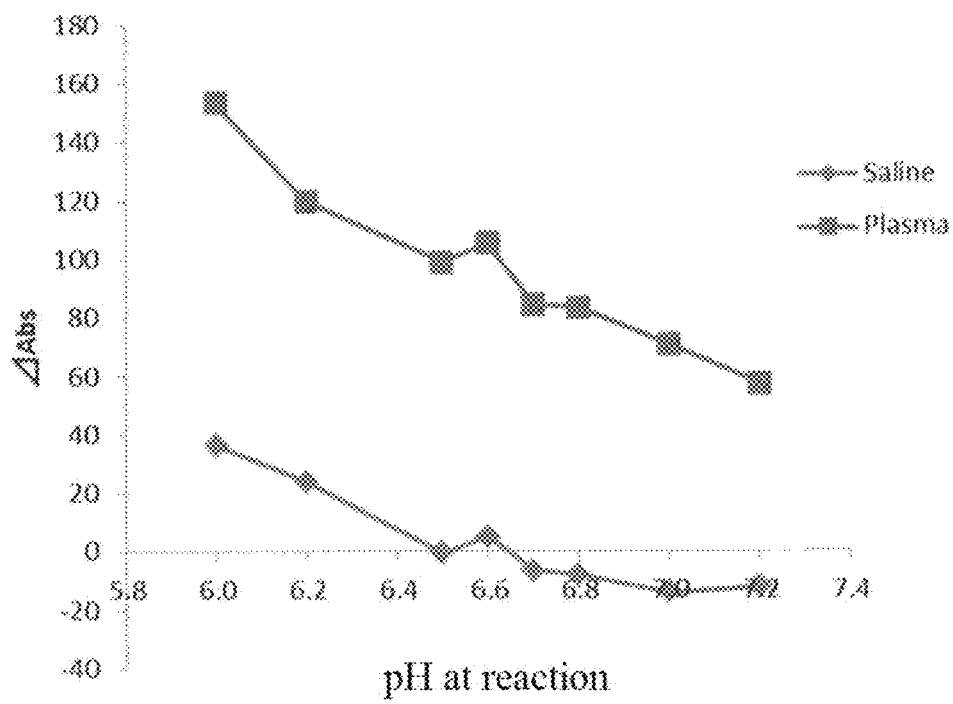
FIG. 6 shows the change in baseline absorbance observed when the pH was changed from 6.0 to 7.2.

A tendency as described below was observed concerning the effect of pH change from 6.0 to 7.2 on the reactivity when Bis-Tris buffer was used as a buffer solution for the first reagent. First of all, a line referred to as the Saline Base went below zero at pH 6.7 (FIG. 6). For the effect on the reactivity to TAT corrected by subtraction of the values of the Plasma Base, a gradually decreasing tendency was observed for the reactivity when the pH was increased (FIG. 7).

Figure 7:
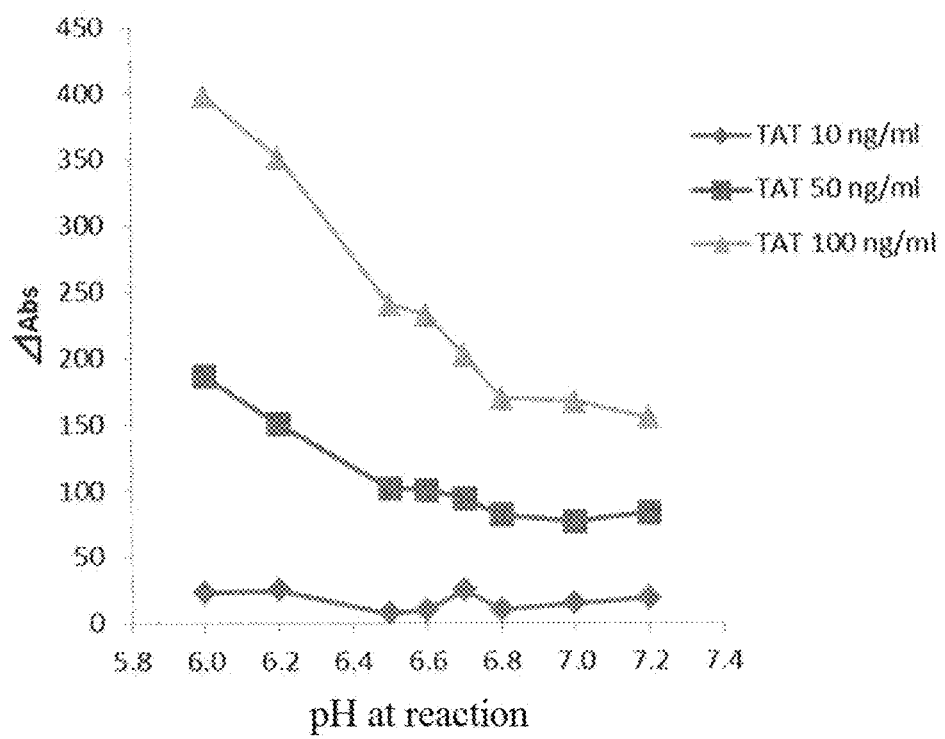
FIG. 7 shows the effect of the change in pH on the reactivity to TAT observed when the pH was changed from 6.0 to 7.2, where the plasma baseline has been subtracted.

Aiming at enhancement of the performance of the reagent to a level allowing highly sensitive measurement of TAT complexes, a signal (ΔAbs) of not less than 100 at a TAT concentration of 50 ng/mL was used as an indicator and then a pH of not more than 6.6 was found to be preferable for the reaction liquid (FIG. 7).

Figure 8:
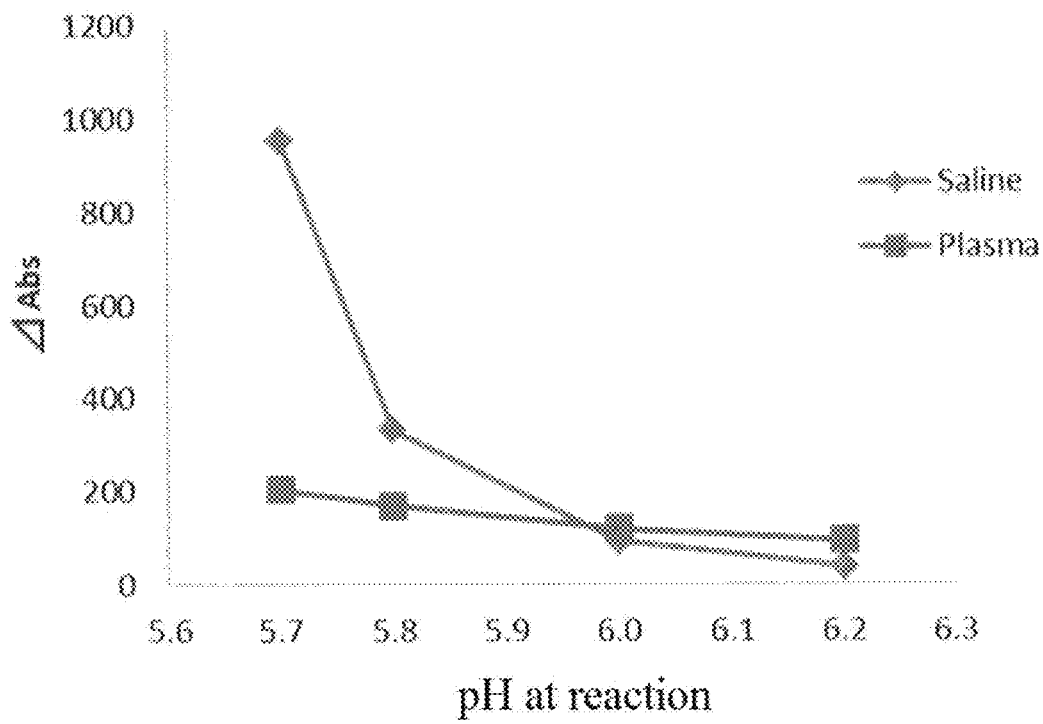
FIG. 8 shows the change in baseline absorbance observed when the pH was changed from 5.7 to 6.2 (where the buffer solution for the first reagent is Bis-Tris buffer).
Figure 9:
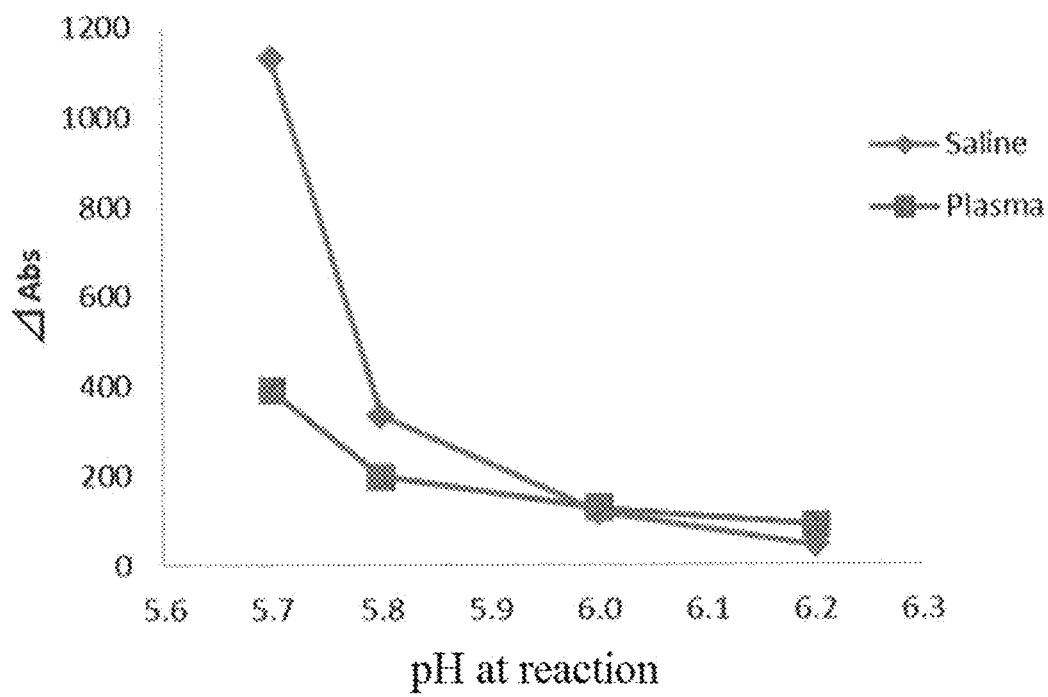
FIG. 9 shows the change in baseline absorbance observed when the pH was changed from 5.7 to 6.2 (where the buffer solution for the first reagent is MES buffer).

Furthermore, the effect of pH change from 5.7 to 6.2 on blank values was examined for the purpose of ensuring the suppression of blank values as well as high reactivity. Consequently, a decreasing tendency was observed for the absorbance of blank samples in the case of using either Bis-Tris or MES buffer when the pH was increased. Particularly, it was found that the decrease in absorbance was large in the pH range of 5.7 to 5.8 and the absorbance went below 100 in the course of pH 6.0 to pH 6.2 (FIGS. 8 and 9).

It was found that the increase in pH tended to decrease the Saline blank value, the Plasma blank value and the reactivity to TAT in a pH-dependent manner. It was a surprising effect found by the inventors that the reactivity was decreased at a pH higher than neutral.

Accordingly, it was found that while the lower limit of the pH was 5.8 and particularly preferably 6.2 in the viewpoint of the suppression of blank values, the upper limit of the pH was 6.6 and particularly preferably 6.2 in the viewpoint of the maintenance of reactivity.

Example 8

Correlation Test Using Clinical Samples

Clinical samples were used to test whether the TAT-measuring latex reagent of the present invention was successfully used for measuring the concentration of TAT complexes in blood.

For the composition of the reagents, reagents prepared as described below were used. A reagent containing 100 mM Bis-Tris, pH 6.2, 700 mM NaCl, 0.05% EMULGEN-150, 0.20% sodium alginate, and 0.15% BSA was used as a first reagent. A second reagent similar to that in Example 7 was used.

The CLEIA reagent was used as a control reagent for the measurement. The TAT calibrator (manufactured by LSI Medience Co.) was used as a standard along with the latex reagent or the CLEIA reagent.

For the samples to be used, 20 samples of citrated plasma were used. To perform the measurement, any of the measuring apparatus and measurement parameters were similar to those in Example 4. The STACIA analyzer (manufactured by LSI Medience Co.) was used as a measuring apparatus for the CLEIA reagent and the measurement was performed in accordance with the parameters described in the package insert.

Figure 10:
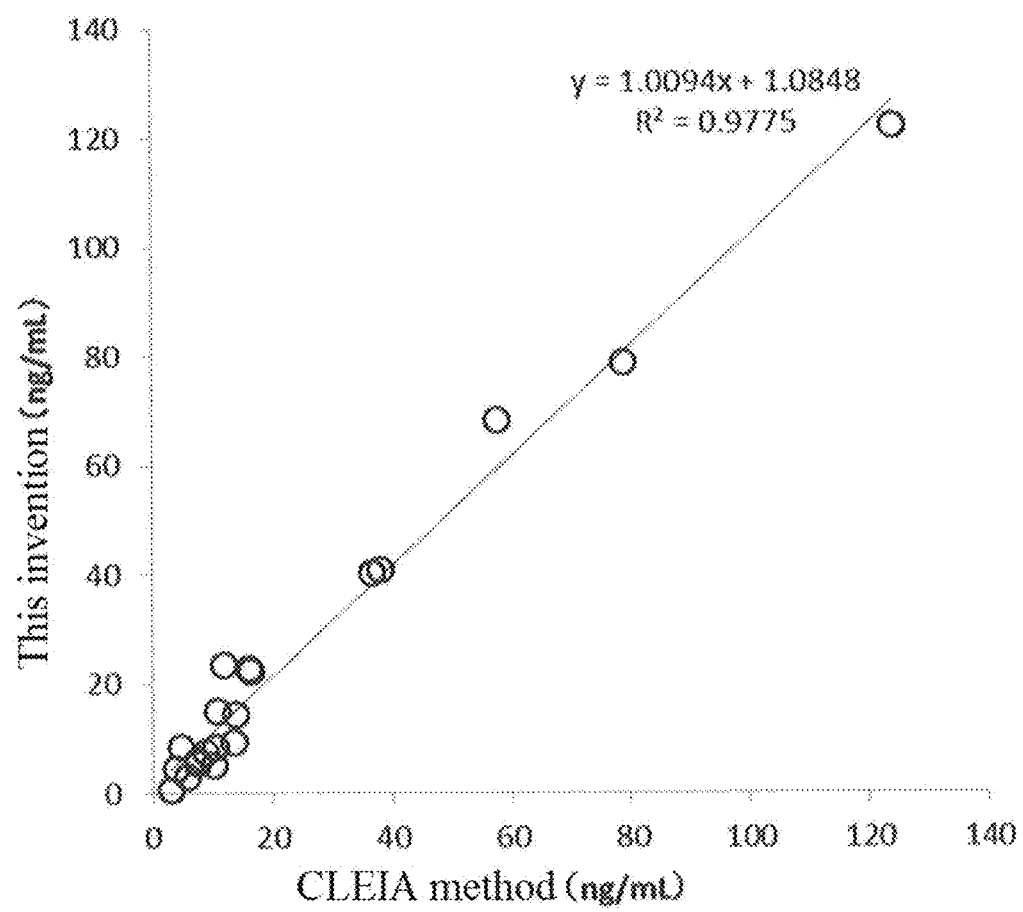
FIG. 10 shows the correlation between the results from the measurement on clinical samples evaluated by using the reagent of the present invention and using CLEIA.

The results of the measurements by both the reagents were presented in FIG. 10.

The latex reagent according to the present invention indicated a good correlation with the assay reagent according to a conventional CLEIA reagent within the range from 3 ng/mL to 120 ng/mL even in the case of using clinical samples. Thus, the use of the present invention enables highly sensitive measurement of clinical samples without treatments such as B/F separation.

What is claimed is:

1. A method for measuring (T)-antithrombin (AT) (TAT) complexes in a sample separated from a living body, comprising:
   (a) performing a latex immunoagglutination reaction under an acidic condition of pH 5.8 to 6.6, comprising contacting the sample with a latex agglutination assay reagent wherein the latex agglutination assay reagent comprises:
      (i) a first antibody bound to a first latex particle, wherein the first antibody binds to the antithrombin part of the TAT complex and recognizes the complex, wherein the first antibody has a reactivity to the TAT complex that is 100 to 50,000 times higher than the reactivity to from antithrombin, and (ii) a second antibody bound to a second latex particle wherein the second antibody binds to the thrombin part of the TAT complex and recognizes the complex; and
   (b) measuring agglutination of latex particles formed by the reaction of the TAT complex, first antibody of (i) and the second antibody of (ii), thereby determining the amount of TAT complexes in the sample.

2. The method according to claim 1, wherein said condition is pH of 6.0 to 6.4.

3. The method according to claim 1, further comprising: contacting the sample with a first reagent comprising a buffer solution at a pH of 5.8 to 6.6 to form a mixture prior to step (a), and wherein performing the latex immunoagglutination reaction under an acidic condition of pH 5.8 to 6.6, comprises contacting the mixture comprising the sample and the first reagent with latex agglutination assay reagent.

* * * * *

UNITED STATES PATENT AND TRADEMARK OFFICE
CERTIFICATE OF CORRECTION

PATENT NO. : 11,237,157 B2
APPLICATION NO. : 16/861040
DATED : February 1, 2022
INVENTOR(S) : Tatsuya Yoshida et al.

It is certified that error appears in the above-identified patent and that said Letters Patent is hereby corrected as shown below:

On the Title Page

Item (56), Column 2, Line 7, under Other Publications, delete "etal.," and insert --et al.,--.

In the Specification

In Column 13, Line 2 (Approx.), delete "polygulcosides," and insert --polyglucosides,--.

In the Claims

In Column 19, Claim 1, Line 16 (Approx.), after "measuring" insert --thrombin--.

In Column 20, Claim 1, Line 6 (Approx.), delete "from" and insert --free--.

In Column 20, Claim 3, Line 22 (Approx.), after "with" insert --the--.

Signed and Sealed this
Nineteenth Day of July, 2022

Katherine Kelly Vidal
*Director of the United States Patent and Trademark Office*